(12) United States Patent
Hoover et al.

(10) Patent No.: US 12,403,000 B2
(45) Date of Patent: Sep. 2, 2025

(54) LIGAMENT FIXATION DEVICE AND METHOD

(71) Applicant: ARTHREX, INC., Naples, FL (US)

(72) Inventors: Timothy R. Hoover, Naples, FL (US); Kenneth T. Helenbolt, Naples, FL (US); Peter S. Borden, Palos Verdes Estates, CA (US); Yasuyuki Ishibashi, Aomori-kan (JP)

(73) Assignee: ARTHREX, INC., Naples, FL (US)

( * ) Notice: Subject to any disclaimer, the term of this patent is extended or adjusted under 35 U.S.C. 154(b) by 263 days.

(21) Appl. No.: 17/867,850

(22) Filed: Jul. 19, 2022

(65) Prior Publication Data

US 2022/0346939 A1  Nov. 3, 2022

Related U.S. Application Data

(60) Continuation of application No. 16/697,679, filed on Nov. 27, 2019, now Pat. No. 11,406,488, which is a
(Continued)

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0404* (2013.01);
(Continued)

(58) Field of Classification Search
CPC ............ A61F 2/0811; A61F 2002/0829; A61F 2002/0835; A61F 2002/0841;
(Continued)

(56) References Cited

U.S. PATENT DOCUMENTS 5,316,476 A  5/1994  Krauser
5,531,792 A * 7/1996  Huene ................... A61F 2/0811
                                                                411/80
(Continued)

OTHER PUBLICATIONS

International Preliminary Report on Patentability for International application No. PCT/US2016/015091 dated Aug. 10, 2017.
(Continued)

*Primary Examiner* — Suzette J Gherbi
(74) *Attorney, Agent, or Firm* — Carlson, Gaskey & Olds, P.C.

(57) ABSTRACT

Systems and methods for providing fixation of soft tissue (for example, ligament) to bone by employing a novel multi-piece device. The novel multi-piece device is a ligament fixation system consisting of a larger collar that is initially impacted into a bone aperture, and a smaller plug/bullet-shaped part that is impacted into the larger collar. During ligament repair/reconstruction, the graft is inserted into a bone tunnel with sutures from the graft extending outside the tunnel. The sutures are passed through a collar of the multi-part device and the collar is then inserted into the bone tunnel. The graft suture strands may be tensioned. Subsequently, the smaller plug/bullet-shaped part is impacted into the collar thereby maintaining the tension on the graft sutures. The plug/bullet-shaped part is tightened after the desired tension on the suture is achieved.

12 Claims, 5 Drawing Sheets

Related U.S. Application Data continuation of application No. 15/835,542, filed on Dec. 8, 2017, now Pat. No. 10,492,901, which is a division of application No. 14/610,395, filed on Jan. 30, 2015, now Pat. No. 9,855,132.

(52) U.S. Cl.
CPC . *A61B 2017/0414* (2013.01); *A61B 2017/044* (2013.01); *A61B 2017/0445* (2013.01); *A61B 2017/0453* (2013.01); *A61B 2017/0458* (2013.01); *A61B 2017/0464* (2013.01); *A61B 2017/0496* (2013.01); *A61F 2002/0829* (2013.01); *A61F 2002/0835* (2013.01); *A61F 2002/0841* (2013.01); *A61F 2002/0852* (2013.01); *A61F 2002/0864* (2013.01); *A61F 2002/0882* (2013.01)

(58) Field of Classification Search
CPC ...... A61F 2002/0852; A61F 2002/0864; A61F 2002/0882; A61B 17/0401; A61B 17/0404; A61B 2017/0414; A61B 2017/044; A61B 2017/0445; A61B 2017/0453; A61B 2017/0458; A61B 2017/0464; A61B 2017/0496
See application file for complete search history.

(56) References Cited

U.S. PATENT DOCUMENTS

| | | | | |
|---|---|---|---|---|
| 6,132,442 | A * | 10/2000 | Ferragamo | A61F 2/0811 |
| | | | | 606/328 |
| 8,696,703 | B2 | 4/2014 | Anspach, III et al. | |
| 8,709,055 | B2 | 4/2014 | Beyar et al. | |
| 9,855,132 | B2 * | 1/2018 | Hoover | A61B 17/0401 |
| 10,492,901 | B2 | 12/2019 | Hoover et al. | |
| 2002/0055780 | A1 | 5/2002 | Sklar | |
| 2003/0050666 | A1 | 3/2003 | Grafton | |
| 2004/0034353 | A1 | 2/2004 | Michelson | |
| 2004/0093031 | A1 | 5/2004 | Burkhart et al. | |
| 2006/0264954 | A1 * | 11/2006 | Sweeney, II | A61B 17/8685 |
| | | | | 606/328 |
| 2007/0055371 | A1 * | 3/2007 | Laghi | A61F 2/5046 |
| | | | | 450/55 |
| 2007/0167950 | A1 | 7/2007 | Tauro et al. | |
| 2009/0198288 | A1 * | 8/2009 | Hoof | A61F 2/0811 |
| | | | | 606/301 |
| 2009/0292321 | A1 | 11/2009 | Collette | |
| 2010/0174369 | A1 | 7/2010 | Wang et al. | |
| 2010/0298936 | A1 | 11/2010 | Shino | |
| 2011/0022066 | A1 * | 1/2011 | Sevrain | A61B 17/86 |
| | | | | 606/151 |
| 2011/0112641 | A1 | 5/2011 | Justin et al. | |
| 2012/0053691 | A1 | 3/2012 | Hays et al. | |
| 2012/0078369 | A1 | 3/2012 | Hart | |
| 2012/0265299 | A1 | 10/2012 | Beck, Jr. et al. | |
| 2013/0013064 | A1 | 1/2013 | West, Jr. | |
| 2013/0090731 | A1 | 4/2013 | Walker | |
| 2014/0276993 | A1 * | 9/2014 | Reilly | D04C 1/06 |
| | | | | 606/151 |
| 2014/0288596 | A1 | 9/2014 | Anspach et al. | |
| 2014/0336760 | A1 * | 11/2014 | Eggli | A61F 2/0811 |
| | | | | 623/13.14 |
| 2015/0012093 | A1 | 1/2015 | Sklar | |
| 2015/0173889 | A1 | 6/2015 | Whittaker | |
| 2015/0272723 | A1 * | 10/2015 | Hristov | A61F 2/12 |
| | | | | 623/8 |
| 2016/0082235 | A1 * | 3/2016 | Mosharrafa | A61M 29/02 |
| | | | | 606/192 |
| 2016/0089231 | A1 | 3/2016 | Donnelly et al. | |
| 2016/0095692 | A1 | 4/2016 | Whittaker | |
| 2016/0100936 | A1 | 4/2016 | Niese et al. | |
| 2016/0120641 | A1 | 5/2016 | Beck, Jr. et al. | |
| 2016/0256259 | A1 * | 9/2016 | Wirth | A61F 2/12 |
| 2018/0221017 | A1 | 8/2018 | Stone | |
| 2019/0247175 | A1 * | 8/2019 | Wang | A61F 2/0063 |
| 2019/0350697 | A1 * | 11/2019 | Algawi | A61L 27/18 |
| 2020/0268503 | A1 * | 8/2020 | Rehnke | A61F 2/12 |
| 2021/0052367 | A1 * | 2/2021 | Yang | A61F 2/12 |

OTHER PUBLICATIONS

Examination report No. 1 for standard patent application, AU Application No. 2016211581, dated Aug. 13, 2019.

Official Action for EP Application No. 16705618.3 dated Jun. 22, 2021.

Canadian Application No. 2,972,993, Office Communication dated Mar. 9, 2022.

\* cited by examiner

LIGAMENT FIXATION DEVICE AND METHOD

CROSS REFERENCE TO RELATED APPLICATIONS

This is a continuation of U.S. patent application Ser. No. 16/697,679, filed on Nov. 27, 2019, which is a continuation of U.S. patent application Ser. No. 15/835,542, filed on Dec. 8, 2017, now U.S. Pat. No. 10,492,901, which is a divisional of U.S. patent application Ser. No. 14/610,395, filed on Jan. 30, 2015, now U.S. Pat. No. 9,855,132, the entire disclosures of which are incorporated by reference herein.

FIELD OF THE INVENTION

The present invention relates to the field of surgery and, more particularly, to a new fixation device for ligament reconstruction.

BACKGROUND OF THE INVENTION

When soft tissue such as ligament or tendon becomes detached from bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone. Knotless suture anchors, such as the two-piece Arthrex PushLock® anchor, disclosed in U.S. Pat. No. 7,329,272, have been developed to facilitate tissue fixation to bone.

There is a need for improved anchor assemblies and constructs, as well as methods of fixating tissue (for example, ligament) within a socket or tunnel of a bone with such improved anchor assemblies. Also needed are methods of tissue fixation wherein suture tension is conducted and maintained initially and before the final fixation of the construct to or into bone. Methods of sealing off a bone aperture/tunnel/socket to contain biologics such as blood, bone marrow, growth factors, etc. are also needed.

SUMMARY OF THE INVENTION

The present invention provides systems and methods for providing fixation of soft tissue (for example, ligament) to bone by employing a novel multi-piece device. The novel ligament fixation device is a multi-piece device consisting of a larger collar that is initially impacted into a bone aperture, and a smaller plug/bullet-shaped part that is impacted into the larger collar.

During ligament repair/reconstruction, the collar is inserted into a bone tunnel and the graft is then inserted through the collar with the graft whip-stitching coming out of the collar. The graft suture strands are tensioned. Subsequently, the smaller plug/bullet-shaped part is impacted into the collar thereby maintaining the tension on the graft sutures. The plug/bullet-shaped part is tightened after the desired tension on the suture is achieved and confirmed by a tensioner, for example. Final fixation is achieved when the ligament sutures are tied over the front of the plug/bullet with the sutures laying in a groove/slot in the plug/bullet. The system can also be used with knotless fixation devices such as Arthrex ACL TightRope® product line.

The novel multi-piece anchor system (TensionLoc™ device) maintains suture tension initially and before final fixation. The device also seals off the aperture/opening of the bone tunnel/socket to contain fluids, blood and/or bone marrow, and impart healing properties to the overall repair. The device may be provided in various sizes, for example, 7 mm, 8 mm, 9 mm, etc.

These and other features and advantages will become apparent from the following description that is provided in connection with the accompanying drawings and illustrated embodiments.

DETAILED DESCRIPTION OF THE PREFERRED EMBODIMENTS

Figure 1:
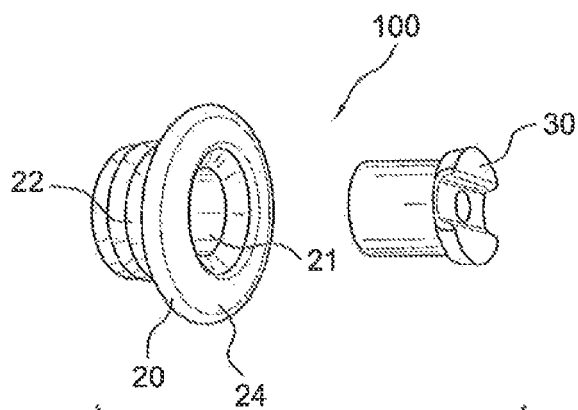
FIG. 1 illustrates an exemplary anchor assembly of the present invention (showing two components in an unassembled state).
Figure 2:
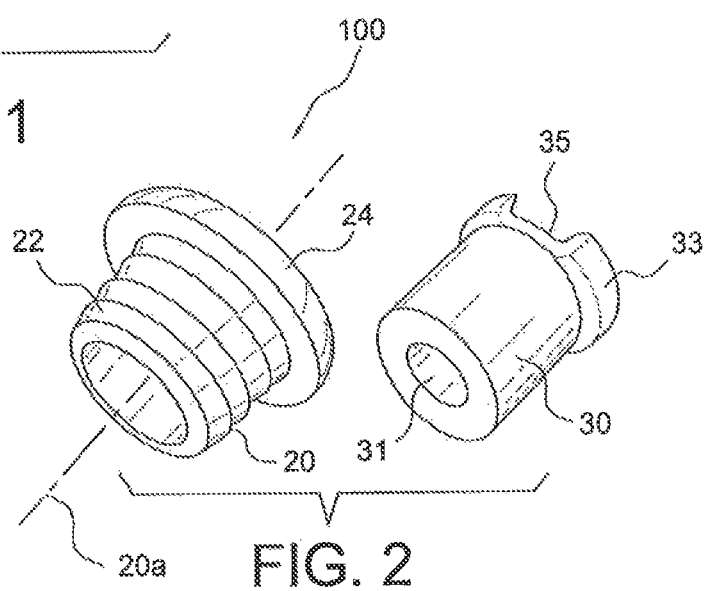
FIG. 2 illustrates an enlarged view of the exemplary anchor assembly of FIG. 1.

The present invention provides surgical systems and methods for knotted and knotless ligament repair and fixation, such as fixation of soft tissue to bone.

The present invention provides improved anchor assemblies and constructs, as well as methods of fixating tissue (for example, ligament) within a socket or tunnel of a bone with such improved anchor assemblies. According to the exemplary methods of the present invention, tissue fixation is achieved wherein suture tensioning is conducted and maintained initially and before the final fixation of the construct to or into bone is achieved. The present invention also provides methods of sealing off a bone aperture/tunnel/socket to contain biologics such as blood, bone marrow, growth factors and healing factors, among many others. The anchor assemblies are multi-piece devices, for example, two- or three-piece devices.

In an exemplary embodiment, and as detailed below, the systems and methods for providing fixation of soft tissue (for example, ligament) to bone employ a novel two-piece device that consists of (i) a larger collar that is initially impacted into a bone aperture; and (ii) a smaller plug/bullet-shaped part that is impacted into the larger collar. During ligament repair/reconstruction, the collar is inserted into a bone tunnel and the graft is then inserted through the collar with the graft whip-stitching coming out of the collar. The graft suture strands are tensioned. Subsequently, the smaller plug/bullet-shaped part is impacted into the collar thereby maintaining the tension on the graft sutures. The plug/bullet-shaped part is tightened after the desired tension on the suture is achieved and confirmed by a tensioner, for example. At least one or both pieces of the two-piece device may be formed of PEEK, composite or metal.

Final fixation is achieved when the ligament sutures are tied over the front of the plug/bullet with the sutures laying in a groove/slot in the plug/bullet. The system can also be used with knotless fixation devices such as Arthrex ACL TightRope® product line.

In additional embodiments, the novel ligament fixation device is a three-piece device consisting of (i) a larger bone tunnel compression device in the form of an outer piece (a "molly") that is provided with external threads or teeth and with at least one tensioning spot; (ii) a smaller threaded, smooth, inner sleeve that is configured to be received within the larger compression device; and (iii) a tapered inner compression screw that is configured to be received within the smaller inner sleeve. At least one or all components of the three-piece device may be formed of PEEK, composite or metal.

The novel TensionLoc™ devices of the present invention maintain suture tension initially and before final fixation. The devices also seals off the aperture/opening of the bone tunnel/socket to contain fluids, blood and/or bone marrow, and impart healing properties to the overall repair. The devices may be provided in various sizes, for example, 7 mm, 8 mm, 9 mm, etc.

The present invention also provides methods of fixation of tissue to tissue (for example, soft tissue to bone) by the steps of: (i) providing a multi-piece anchor construct including at least a first piece in the form of a large collar and a second piece in the form of a plug; (ii) inserting a graft through into a bone socket or tunnel so that sutures attached to the graft exit an aperture of the bone socket or tunnel; (iii) sliding the first piece over the graft sutures and securing the first piece into the bone aperture (for example, by impacting the first piece into the bone aperture); (iii) subsequently, tensioning the graft by pulling on the suture strands; (iv) subsequently, inserting the second piece into the first piece (for example, by impacting the second piece into the first piece) while maintaining the tension on the graft sutures; (v) tensioning the graft sutures and tying graft sutures over the front of the second piece; and (vi) securing the graft sutures into at least a groove/slot of the second piece to achieve final fixation.

Referring now to the drawings, where like elements are designated by like reference numerals, FIGS. 1-13 illustrate exemplary anchor (anchoring) systems or constructs 100, 200 of the present invention for securement into bone hole 88 formed within bone 80 and for fixation of tissue 90 within such hole formed within bone 80, to achieve tissue repair 99.

Constructs 100, 200 are multi-piece or multi-part anchor systems, for example, a two-piece construct 100 or a three-piece construct 200. An exemplary two-piece anchor 100 includes a first piece 20 (first component 20) and a second piece 30 (second component 30) that is inserted within the first piece 20. As shown in FIGS. 1-4, the first component 20 is a cannulated fixation device in the form of a collar provided with outer threads 22 or similar structures (for example, barbs, teeth, etc.) and a ridge 24. Full cannulation 21 extends along longitudinal axis 20 *a* of the component 20 and has an inner diameter d1.

Second component 30 is also a cannulated fixation device which is in the form of a plug/bullet designed to be inserted within cannulation 21 of the first component 20 and securely engage the inner surface/walls of the cannulation 21. Second component 30 is provided with a smooth cylindrical outer wall that allows easy insertion through the collar 20 (first component 20) and has a full cannulation 31 (to allow passage of tissue and suture strands, as detailed below). At least one groove/slot 35 is also provided within a plug collar 33 in the second component 30.

Figure 3:
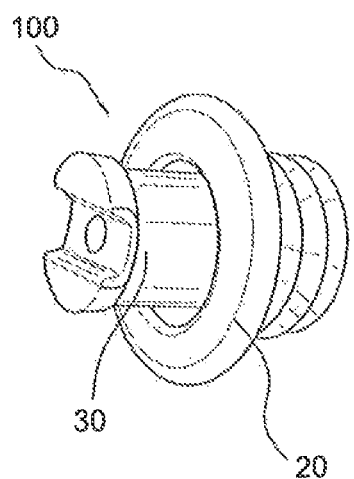
FIG. 3 illustrates the exemplary anchor assembly of FIG. 1 with the components in the assembled state.
Figure 4:
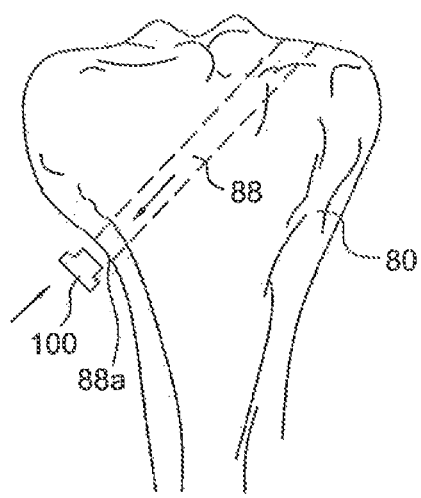
FIG. 4 illustrates the exemplary anchor assembly of FIG. 3 in the vicinity of a bone tunnel or socket.

Outer diameter d2 of the second component 30 is about equal to inner diameter d1, to allow secure and tight engagement of the second component 30 within the first component 20 and obtain assembly 100 (FIG. 3). The length of the first component 20 is about equal to that of the second component 30 so that, when the two components are engaged with/impacted within each other, the plug collar 33 of the second component 30 is flush with ridge 24 of the first component 20.

At least one or the components 20, 30 of the two-piece device 100 may be formed of PEEK, composite or similar material, or metal.

During ligament repair/reconstruction, the graft is first inserted and positioned within a bone tunnel 88 (FIG. 4) with the sutures for the graft whip-stitching coming out of the bone tunnel. Sutures from the graft are then inserted into the collar 20 and the collar 20 is inserted/impacted into the bone tunnel 88 (FIG. 4) with the graft sutures for whip-stitching coming out of the collar. The graft suture strands are tensioned. Subsequently, the smaller plug/bullet-shaped part 30 is impacted into the collar 20 thereby maintaining the tension on the graft sutures. The plug/bullet-shaped part 30 is tightened after the desired tension on the suture is achieved and confirmed by a tensioner, for example. Final fixation is achieved when the ligament sutures are tied over the front of the plug/bullet 30 with the sutures laying in groove/slot 35 in the plug/bullet 30.

The present invention also provides methods of fixation of tissue to tissue (for example, soft tissue to bone) by inter alia the steps of: (i) providing a multi-part or multi-piece construct 100 including a first piece 20 in the form of a large collar and a second piece 30 in the form of a plug/bullet; (ii) positioning tissue graft within a bone tunnel or socket 88 formed into bone 80 with sutures/flexible strands coming out of aperture 88 *a* of the bone socket or tunnel 88; (iii) sliding the first piece 20 over the flexible strands/sutures and inserting the first piece 20 through the bone aperture 88 *a* and into the bone tunnel or socket 88 (by impacting, for example, the first piece 20 into the bone aperture 88 *a*); (iv) subsequently, tensioning the graft by pulling on the suture strands; (v) inserting the second piece 30 into the first piece 20 (by impacting, for example, the second piece 30 into the first piece 20) while maintaining the tension on the graft sutures; and (vi) tying graft sutures over the front of the second piece 30 and securing the graft sutures into at least a groove/slot 35 of the second piece 30 to achieve final fixation.

Figure 5:
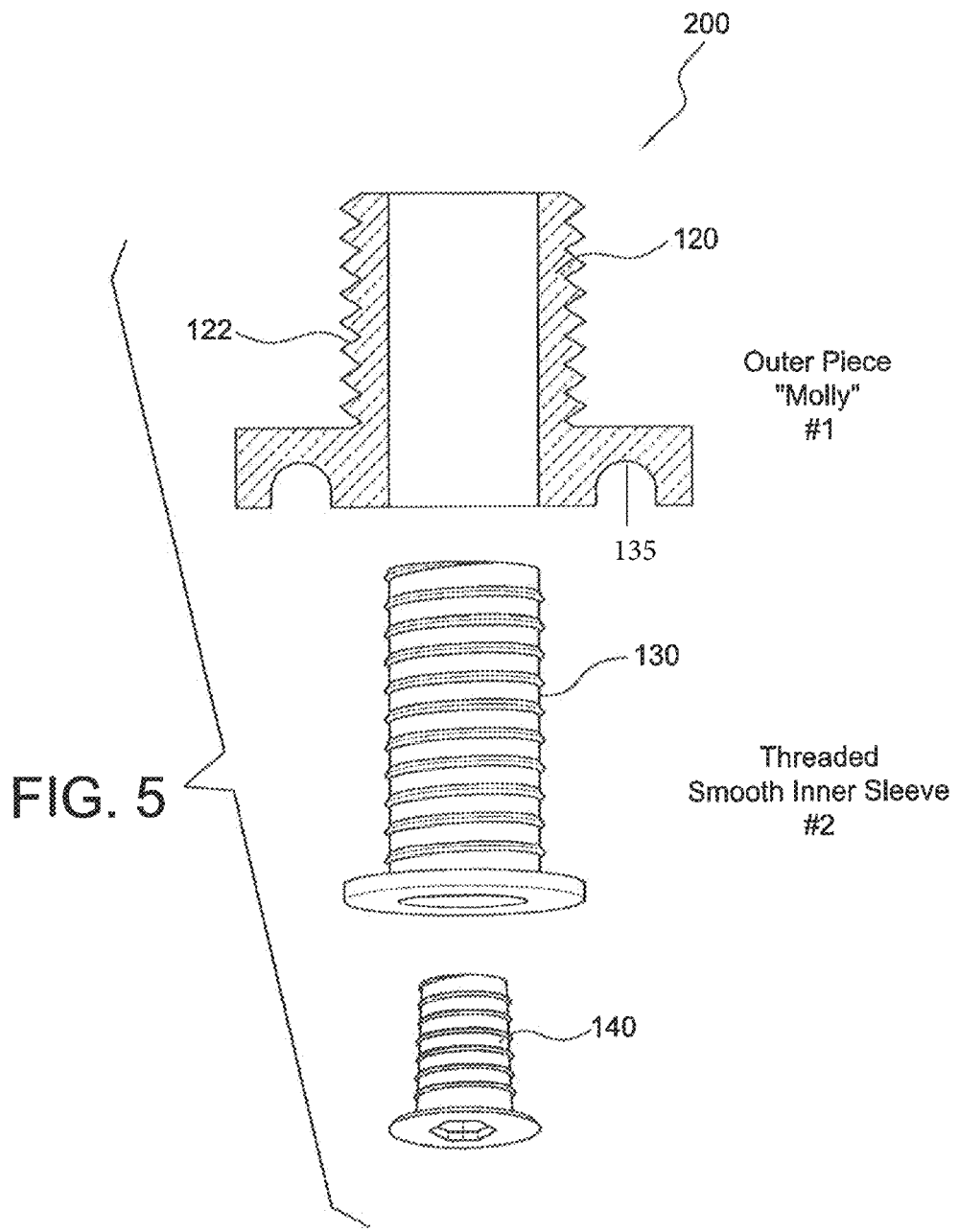
FIG. 5 illustrates another exemplary anchor assembly of the present invention (showing three components in an unassembled state).

FIG. 5 illustrates another exemplary embodiment of a multi-part construct 200 in the form of ligament fixation device 200 of the present invention. The three-piece construct 200 is a three-part anchor system consisting of (i) a larger bone tunnel compression device in the form of an outer piece 120 (a "molly") that is provided with external threads 122 or teeth and with at least one tensioning spot/groove/slit 135; (ii) a smaller threaded, smooth, inner sleeve 130 that is configured to be received within the larger bone compression device 120; and (iii) a tapered inner compression screw 140 that is configured to be received within the smaller inner sleeve 130. Optionally, the system 200 also includes (iv) a tensioner 150. At least one or all components 120, 130, 140 of the three-piece device 200 may be formed of PEEK, composite or metal.

An exemplary method of tissue repair or reinforcement with exemplary multi-part construct 200 of the present invention comprises inter alia the following steps: (i) outer piece is inserted into tibial tunnel (similar to a "molly," this piece expands against the inner tunnel with "teeth" grabbing cancellous bone); (ii) sutures from ACL graft are brought out tunnel as the second piece 130 (smaller inner sleeve 130) is inserted; and (iii) screw is then tightened after tensioner confirms desired suture tension.

The anchor system 100, 200 of the present invention has applicability to any tissue repair and reconstructions, for example, any attachment of a tissue graft to bone or any ligament or graft repair and reconstruction, including knee and shoulder repairs but also small joint repairs of hand and wrist applications such as scapholunate repair, and foot and ankle repairs such as lateral ankle, Achilles tendon repair and tendon reattachment.

A method of tissue fixation according to the present invention comprises inter alia the steps of: (i) providing flexible strands such as suture strands; (ii) securing the flexible strands to the tissue to be fixated; (iii) securing the tissue into a bone tunnel or socket so that the flexible strands exit an aperture of the bone tunnel or socket; (iv) sliding the flexible strands through a first part of a multi-part construct, and anchoring the first part into bone; (v) tensioning the flexible strands through the first part of the multi-part construct; (vi) anchoring a second part of the multi-part construct into the first part and into bone; and (vii) tensioning the flexible strands and securing the flexible strands to the second part.

Figure 10:
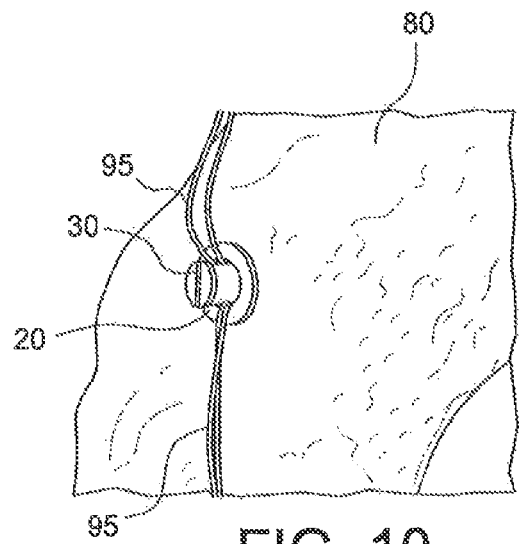
Figure 11:
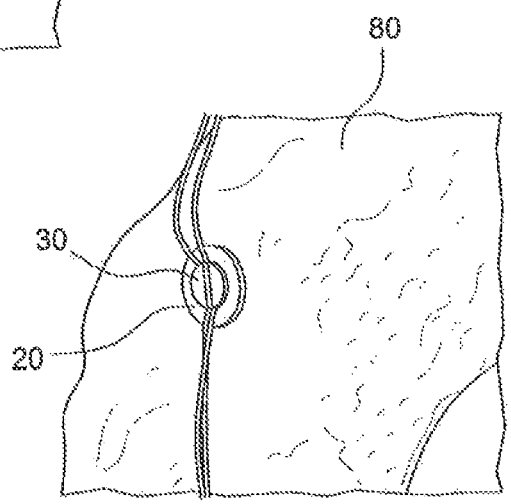
Figure 12:
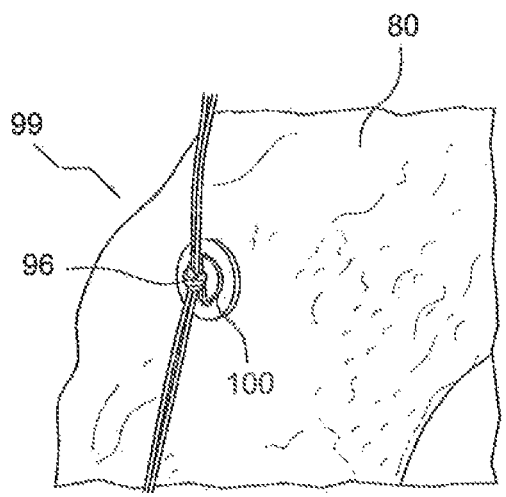

FIGS. 6-12 illustrate subsequent steps of a method of tissue fixation with the exemplary anchor assembly 100 of FIG. 3 and according to an exemplary embodiment of the present invention, to achieve final repair 99 (FIG. 12).

Figure 6:
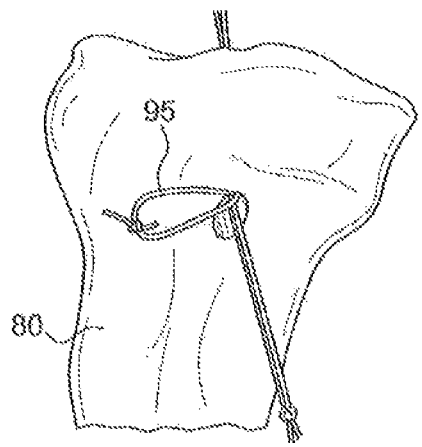
FIGS. 6-12 illustrate subsequent steps of a method of tissue fixation with the exemplary anchor assembly of FIG. 3 and according to an exemplary embodiment of the present invention.

FIG. 6: after graft 90 has been inserted and fixed into femur 82, the anchor assembly 100 will be applied.

Figure 7:
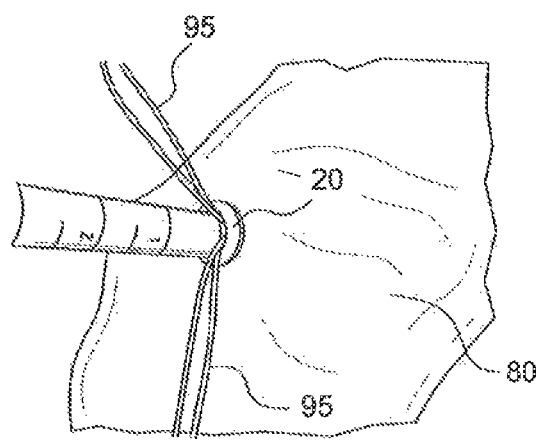

FIG. 7: Insert the collar 20 of the anchor assembly 100 over the graft sutures 95, and impact into tibia 80 until flush.

Figure 8:
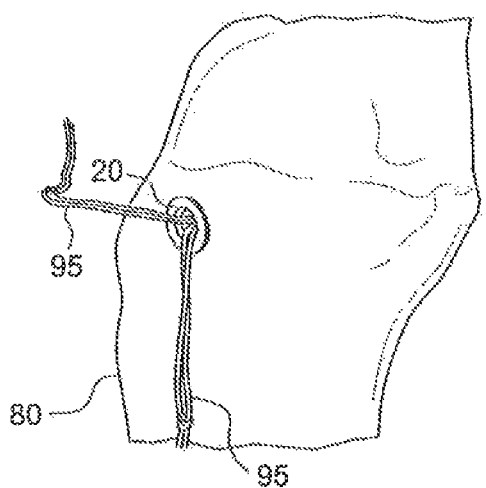

FIG. 8: note the final flush seating of collar 20 to bone 80 and orientation of sutures 95 are 12 and 6 o'clock.

Figure 9:
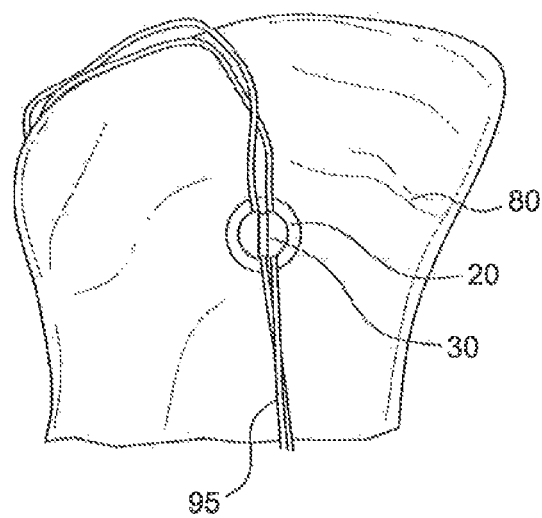

FIG. 9: to insert plug 30 of the anchor assembly 100, begin by ensuring orientation of sutures 95 must be at 12 and 6 o'clock, as shown.

FIG. 10: put sutures under tension and impact plug into collar with sutures still at 12 and 6 o'clock to flush.

FIG. 11: final flush seating of plug 30 to collar 20 to maintain initial suture tension (note suture position).

FIG. 12: final fixation is achieved by tying suture strands 95 together to form knot 96 and so the strands 95 sit into slot 35 of the plug 30. Loose suture ends can now be trimmed without disturbing knot construct and final repair 99.

Figure 13:
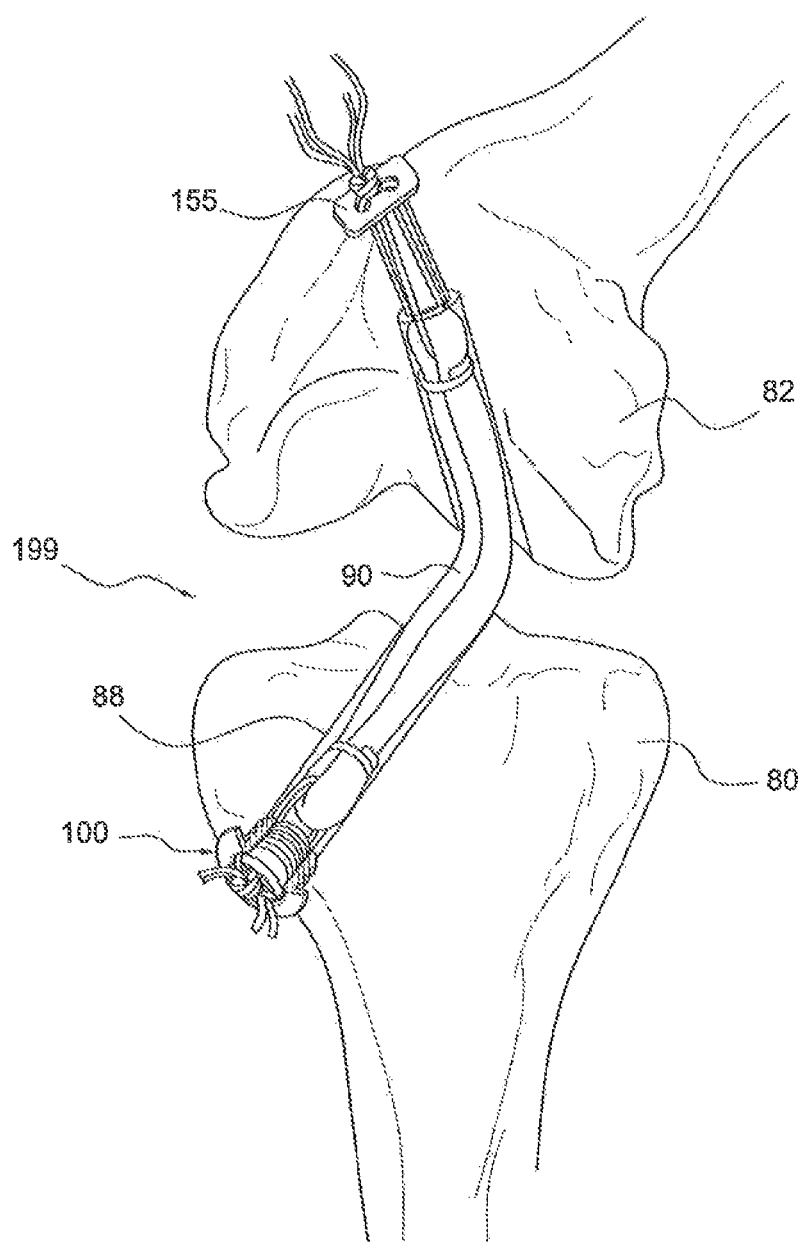
FIG. 13 is a schematic view of a tissue repair with the exemplary anchor assembly of FIG. 3 and according to an exemplary embodiment of the present invention (with a TightRope® device).

FIG. 13 illustrates a schematic view of another tissue repair 199 with the exemplary anchor assembly 100 of FIG. 3 (TensionLoc™ 100) and according to an exemplary embodiment of the present invention, i.e., with a TightRope® device 155. Graft 90 extends within the femoral and tibial sockets formed within femur 82 and tibia 80, and is secured to the bones by TightRope® device 155 and TensionLoc™ 100.

The fixation devices of the present invention advantageously minimize or eliminate the need to tie knots. The use of such multi-part anchors also provides secure fixation of the suture construct, the secure suture construct resulting from the suture being pushed into a hole and held tightly by anchors.

The multi-part anchor systems of the present invention also provide the following additional advantages: accelerate tensioning to desired preference; plugs bone tunnel (for example, the tibial tunnel) holding in fluids that are critical to healing; less invasive with decreased morbidities (i.e., fractures); eliminates "plate prominence" and need for HWR; the preferred PEEK material of the device allows for easy removal if revision surgery is required; and is provided in various sizes, 7 mm, 8 mm, 9 mm, 10 mm, 11 mm, etc.

In the preferred embodiment of the present invention, as mentioned above, suture or suture tape is used with the anchor to fix tissue to bone. However, the multi-piece anchor constructs of the present invention can be used with any type of flexible material or suture, for example FiberWire® or FiberTape® or FiberChain®. In another embodiment, an allograft or biological component may be used instead of suture or tape. The allograft or biological component may be comprised of tendon or pericardium, for example, which provides improved tissue repair. In yet additional embodiments, any combination of suture, suture tape, suture chain, and allograft or biological component may be employed, depending on the characteristics of the specific surgical repair and/or as desired.

At least a portion of the flexible strand may be made of any known suture material, such as cord-like suture, braided suture, or ultrahigh molecular weight polyethylene (UHMWPE) or the FiberWire® suture (disclosed in U.S. Pat. No. 6,716,234 which is hereby incorporated by reference in its entirety). In certain applications and if desired, the flexible strand may also contain suture tape (for example, a collagen stuffed suture tape) or a combination of suture and tape, a stiff material, or combination of stiff and flexible materials, depending on the intended application.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed is:

1. A multi-part anchor system, comprising:
an outer piece;
a sleeve received within the outer piece; and
a tapered part received within the sleeve,
wherein the sleeve and the tapered part cooperate to hold a flexible strand for securing the flexible strand relative to a bone,
wherein each of the outer piece, the sleeve, and the tapered part includes a collar portion and a cylindrical portion that extends from the collar portion,
wherein the collar portion of the outer piece includes at least one tensioning spot, groove, or slit.

2. The multi-part anchor system as recited in claim 1, wherein the sleeve is received within a first cannulation of the outer piece, and the tapered part is received within a second cannulation of the sleeve.

3. The multi-part anchor system as recited in claim 2, wherein at least a portion of the flexible strand is received within the second cannulation.

4. The multi-part anchor system as recited in claim 1, wherein an outer surface of the sleeve is configured to engage an inner surface of the outer piece.

5. The multi-part anchor system as recited in claim 1, wherein the outer piece includes external threads or teeth adapted to engage a bone tunnel wall of the bone.

6. The multi-part anchor system as recited in claim 1, wherein the sleeve includes a smooth inner surface.

7. The multi-part anchor system as recited in claim 1, wherein the sleeve includes a first section having a first outer diameter and a second section having a second outer diameter that is less than the first outer diameter.

8. The multi-part anchor system as recited in claim 1, wherein at least one of the outer piece, the sleeve, or the tapered part is comprised of a PEEK material.

9. The multi-part anchor system as recited in claim 1, wherein each of the outer piece, the sleeve, and the tapered part is comprised of a PEEK material.

10. The multi-part anchor system as recited in claim 1, wherein the cylindrical barrel portion of each of the outer piece, the sleeve, and the tapered part is threaded.

11. The multi-part anchor system as recited in claim 1, wherein the collar portion includes a first outer diameter, and the cylindrical barrel portion includes a second outer diameter that is less than the first outer diameter.

12. The multi-part anchor system as recited in claim 1, wherein the outer piece includes a first length and the tapered part includes a second length that is less than the first length.

* * * * *